US005720760A

United States Patent [19]
Becker et al.

[11] Patent Number: 5,720,760
[45] Date of Patent: Feb. 24, 1998

[54] ENDOSCOPIC OR OPEN LIPECTOMY INSTRUMENT

[75] Inventors: Daniel G. Becker, Chicago, Ill.; Charles W. Gross, Ivy, Va.; Michael P. Glowa, St. Petersburg, Fla.

[73] Assignee: Linvatec Corporation, Largo, Fla.

[21] Appl. No.: 795,436

[22] Filed: Feb. 5, 1997

Related U.S. Application Data

[62] Division of Ser. No. 626,708, Apr. 1, 1996.

[51] Int. Cl.⁶ .................................................. A61B 17/14
[52] U.S. Cl. .......................................... 606/180; 606/167
[58] Field of Search ................................. 606/180, 171, 606/170, 159, 167

[56] References Cited

U.S. PATENT DOCUMENTS

| | | |
|---|---|---|
| 1,663,761 | 3/1928 | Johnson . |
| 2,721,555 | 10/1955 | Jenney . |
| 3,618,611 | 11/1971 | Urban . |
| 3,945,375 | 3/1976 | Banko . |
| 4,203,444 | 5/1980 | Bonnell et al. . |
| 4,577,629 | 3/1986 | Martinez . |
| 4,589,414 | 5/1986 | Yoshida et al. . |
| 4,598,710 | 7/1986 | Kleinberg et al. . |
| 4,603,694 | 8/1986 | Wheeler . |
| 4,674,502 | 6/1987 | Imonti . |
| 4,735,605 | 4/1988 | Swartz . |
| 4,811,734 | 3/1989 | McGurk-Burleson . |
| 4,815,462 | 3/1989 | Clark . |
| 4,834,729 | 5/1989 | Sjostrom . |
| 4,844,088 | 7/1989 | Kambin . |
| 4,850,354 | 7/1989 | McGurk-Burleson . |
| 4,867,155 | 9/1989 | Isaacson . |
| 4,867,157 | 9/1989 | McGurk-Burleson . |
| 5,074,841 | 12/1991 | Ademovic et al. . |
| 5,084,052 | 1/1992 | Jacobs . |
| 5,112,299 | 5/1992 | Pascaloff . |
| 5,176,628 | 1/1993 | Charles et al. . |
| 5,269,798 | 12/1993 | Winkler . |
| 5,275,609 | 1/1994 | Pingleton et al. . |
| 5,284,472 | 2/1994 | Sussman et al. . |
| 5,286,253 | 2/1994 | Fucci . |
| 5,364,395 | 11/1994 | West, Jr. ............................ 606/170 |
| 5,411,514 | 5/1995 | Fucci et al. ........................ 606/180 |
| 5,423,844 | 6/1995 | Miller . |
| 5,474,532 | 12/1995 | Steppe . |
| 5,514,086 | 5/1996 | Parisi et al. . |
| 5,569,178 | 10/1996 | Henley . |

FOREIGN PATENT DOCUMENTS

| | | |
|---|---|---|
| 437932 | 11/1926 | Germany . |
| WO 89/02250 | 3/1989 | WIPO . |

OTHER PUBLICATIONS

Article Entitled "The Soft–Tissue Shaving Procedure For Removal of Adipose Tissue", by Charles W. Gross, M.D. et al., Arch Otolaryngol Head Neck Surg, vol. 121, Oct. 1995, pp. 1117–1120.

Cosmetic Surgery Equipment & Accessories, Anthony Products, Inc. Indianapolis, IN., Two Pages.

Primary Examiner—Michael Buiz
Assistant Examiner—Kevin Truong
Attorney, Agent, or Firm—Gene Warzecha

[57] ABSTRACT

A single surgical instrument capable of being used as a powered resection instrument or a conventional liposuction cannula. The instrument is elongated and may be used in either open or closed (endoscopic) lipectomy procedures, with or without visualization. The instrument comprises a stationary elongated outer tube having a side-facing window near its distal tip and a rotatable elongated inner tube situated within the outer tube and having a cutting edge juxtaposed adjacent the window of the outer tube. The method of using the device comprises the steps of utilizing it as a powered resecting instrument, in which the uniquely shaped surfaces of the inner edge and outer window cooperate to resect tissue, or as a liposuction cannula in which the inner member is stopped in alignment with the outer window.

6 Claims, 2 Drawing Sheets

ENDOSCOPIC OR OPEN LIPECTOMY INSTRUMENT

This is a divisional application of application Ser. No. 08/626,708, filed Apr. 1, 1996.

BACKGROUND OF THE INVENTION

1. Field of the Invention

The invention relates generally to powered surgical cutting instruments for endoscopic use. More particularly, the invention relates to elongated surgical instruments in which an elongated hollow inner tube is rotatably received within a stationary, elongated hollow outer tube, both inner and outer tubes having cutting apertures at their distal ends which cooperate to resect or otherwise affect tissue during endoscopic surgical procedures.

2. Description of the Prior Art

The use of both liposuction and lipectomy devices is known although prior to this invention the use of liposuction, i.e., manual instruments, has been preferred because of deficiencies associated with the prior art lipectomy, i.e., powered systems.

In conventional liposuction procedures, an elongated cannula having a side facing aperture at its distal tip is connected at its proximal end to a source of suction. The cannula is passed through an incision in the body in order to place its distal tip adjacent a body region targeted for removal of fat or adipose tissue. Such manual procedures require vigorous back and forth motion of the cannula in order to avulse fat tissue and aspirate it through the lumen of the cannula.

A powered, lipectomy device is described in U.S. Pat. No. 4,735,605 (Swartz), incorporated by reference herein, in which a conventional manual liposuction cannula is modified by combining it with a rotating inner tube having a cutting edge in the form of a spiral slot in its distal end. The rotation of the slot of the inner tube under the elongated side-facing aperture or window of the cannula creates a "traveling hole" by which tissue sucked into the aperture is resected and aspirated through the lumen of the inner tube with less difficulty than manual procedures. Such powered lipectomy devices have not been widely accepted among surgeons although elongated powered surgical instruments are known to be used in other surgical procedures such as arthroscopy, or more generally, endoscopy.

The term "endoscopic" as used herein refers to closed surgery in which access to the surgical site is gained via one or more portals in the body (natural or artificially created) whether or not one uses a visualization instrument such as an elongated scope or camera. Thus, the lipectomy and liposuction procedures described herein will occasionally and interchangeably be referred to as endoscopic procedures. It will be understood, however, that both lipectomy and liposuction procedures may be performed as open procedures and the invention is intended to provide such flexibility. Open liposuction would, however, require greater suction and the invention enables procedures to be performed with less suction.

Some conventional endoscopic surgical resecting instruments for use in closed surgery (known as shavers or blades) are somewhat similar to the Swartz device: i.e., a straight, elongated stationary outer tubular member having a straight, elongated rotating inner tubular member concentrically disposed in the outer tubular member. The distal ends of the tubes may be formed with a variety of cutting edges and windows to achieve particular functions. Therefore, while many different configurations of inner and outer members are known, those configurations most similar to the Swartz device and most adaptable to use in removing fat or adipose tissue are the ones having a side facing window in the outer member with a cutting edge on the inner member that can resect tissue presented in the outer cutting window. An example of a lipectomy device which is similar to conventional side-facing arthroscopic shavers is shown in U.S. Pat. No. 4,815,462 (Clark). However, known side-facing rotatable shavers are not entirely suitable for use in lipectomy or liposuction procedures; they are generally either too aggressive or ineffective for adipose tissue.

Furthermore, it has been found that a preferred surgical lipectomy procedure, whether open or closed, incorporates lipectomy interchangeably with liposuction. Lipectomy is defined herein as resecting adipose tissue from a surgical site either under direct vision (i.e., open) or endoscopically (with or without visualization) while liposuction is defined herein as aspirating adipose tissue from the site. No known device is optimized for use in both lipectomy and liposuction procedures. Thus, it is an object of this invention to provide a single endoscopic instrument suitable for use as a lipectomy device and as a liposuction device.

There is a need to improve the design of prior art endoscopic surgical shavers to optimize them for use in lipectomy or liposuction procedures. It is generally preferable to sometimes avulse tissue from a site (as in liposuction) rather than resect it (as in lipectomy) in order to avoid inadvertently injuring adjacent structures (e.g. neurovascular bundles, etc.). However, the simple avulsion provided by conventional liposuction cannulas is sometimes too cumbersome, inefficient and traumatic while the resection provided by conventional shavers is sometimes too traumatic and risky.

Accordingly it is an object of this invention to produce a surgical cutting instrument adapted for use in lipectomy and liposuction procedures.

It is also an object of this invention to produce a surgical instrument capable of being used as a conventional manual liposuction cannula as well as a powered lipectomy resecting instrument.

It is another object of this invention to produce a surgical instrument optimized for use in lipectomy and liposuction procedures.

SUMMARY OF THE INVENTION

These and other objects of the invention are achieved by the preferred embodiment disclosed herein which is a surgical resection instrument for use with a powered handpiece comprising an elongated outer tubular member having a generally rounded distal end and a proximal end with a hub for fixed attachment to the handpiece. The outer member has a first, side-facing rectangular cutting window spaced a predetermined distance from its distal end. The window is an opening formed by a first transverse edge extending diametrically across the outer member, a second transverse edge parallel to and longitudinally spaced from the first transverse edge and equal in length thereto, a third, longitudinally extending edge joining corresponding ends of the first and second transverse edges and a fourth, longitudinally extending edge parallel to and transversely spaced from the third edge and equal in length thereto. An elongated inner tubular member is received within the outer tubular member and has a generally rounded distal end and a proximal end with a hub for rotatable attachment to the handpiece. The inner member has a second, side-facing rectangular cutting window spaced a predetermined distance from its distal end. Both first and second rectangular cutting windows are symmetrical to and situated adjacent each other although when aligned the edges of the inner window are recessed from the edges of the outer to permit manual use.

In another aspect the invention is a method of removing adipose tissue from a surgical site using a surgical instrument adapted for use as a liposuction or powered lipectomy device. The method comprises the steps of providing a rotary powered surgical instrument having an elongated inner tube with a first distal cutting window rotatable within an elongated outer tube with a second distal cutting window. The method further comprises rotating the inner tube within the outer tube, stopping the rotation of the tube within the outer with the windows aligned and operating the assembly as a liposuction cannula.

DESCRIPTION OF THE PREFERRED EMBODIMENT

Figure 1:
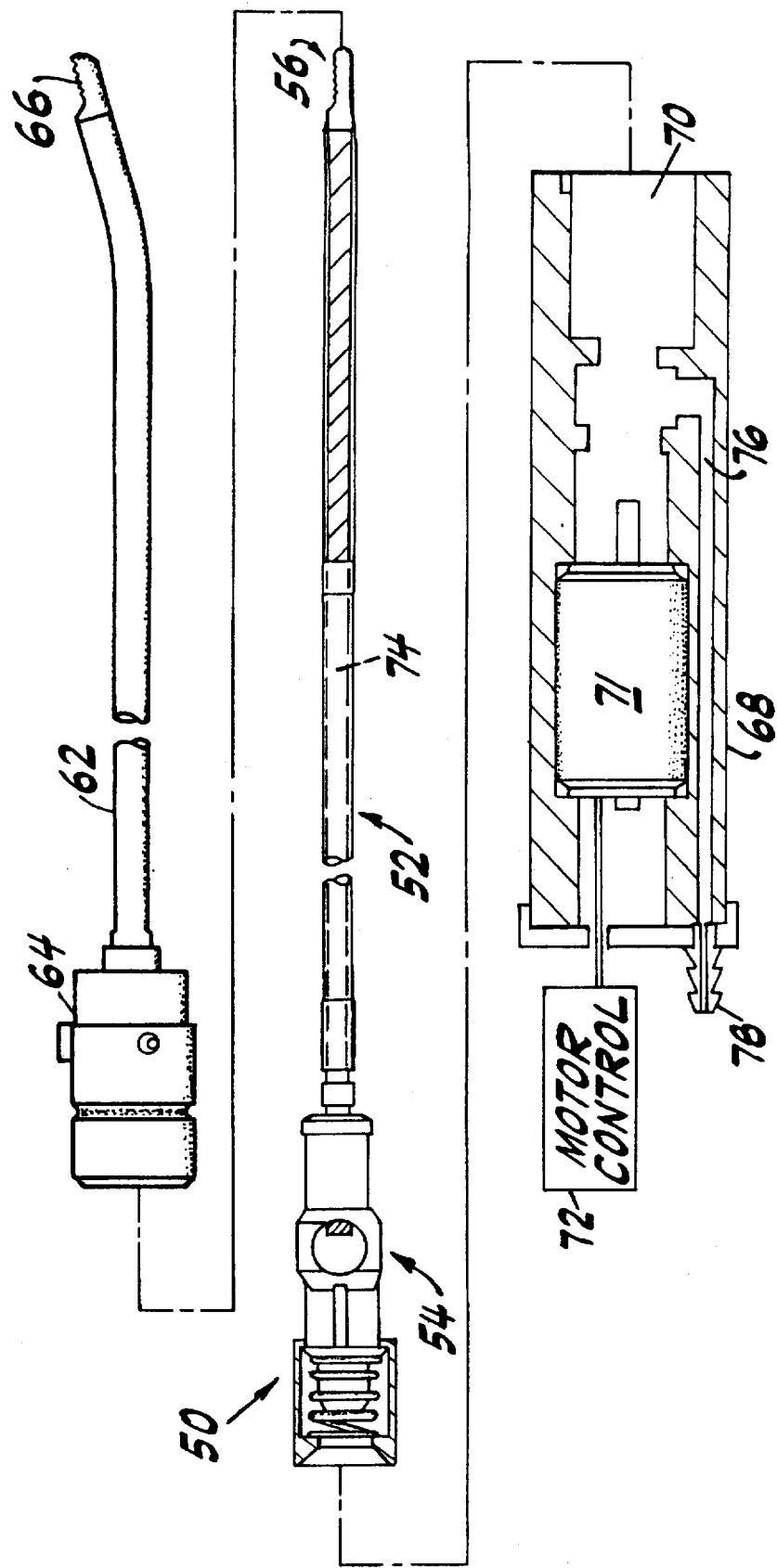
FIG. 1 is a diagrammatic representation, partly in cross-section, of a prior art endoscopic shaver blade and handpiece.

As shown in FIG. 1, a prior art endoscopic resecting instrument comprises a shaver blade assembly 50 having an elongated rotatable inner member 52 with a hub 54 at its proximal end and a cutting tip 56 at its distal end. The inner member fits within a stationary elongated outer member 62 having a hub 64 at its proximal end and a cutting window 66 at its distal end. Inner and outer members 52, 62 are assembled and received in handpiece 68 at its distal end in aperture 70. The shaver blade assembly 50 is held within the handpiece so that the inner member 52 may be rotated by a motor 71 in the handpiece under motor control 72 while resected tissue passes through lumen 74 of the inner member and through handpiece aspiration channel 76 to suction port 78. While shaver blade assembly 50 is shown in FIG. 1 as an angled instrument in which the distal ends of the inner and outer members are able to be bent relative to their proximal ends, it will be understood that the invention described herein may be produced in either an angled configuration or a fixed, straight configuration. A more complete explanation of the prior art endoscopic resection instrument shown in FIG. 1 is given in U.S. Pat. No. 5,286,253 (Fucci), assigned to the assignee hereof and incorporated by reference herein.

Figure 2:
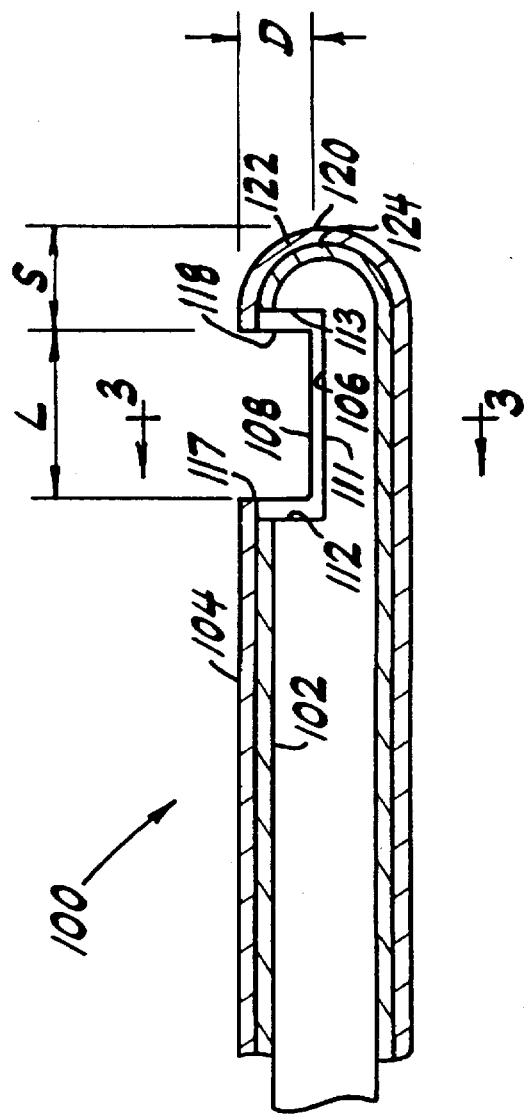
FIG. 2 is a diagrammatic cross-sectional view of the distal tip of a lipectomy blade constructed in accordance with the principles of this invention.
Figure 3:
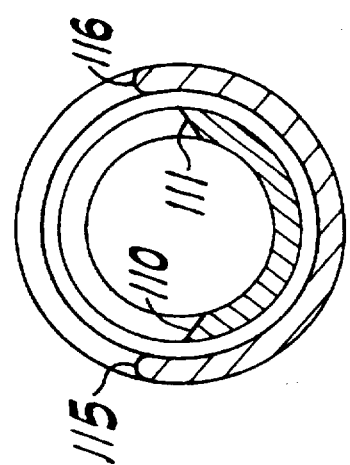
FIG. 3 is a cross-sectional view of FIG. 2 taken along the lines 3—3.

The present invention is an improvement over the prior art system and, for explanation purposes will be referred to as liposhaver blade 100 best seen in FIGS. 2 and 3. Blade 100 comprises an elongated inner member 102 and an elongated outer member 104. It will be understood that the proximal end of assembly 100 (not shown) is conventional and similar to the structure described in FIG. 1.

Inner and outer members 102, 104 have rectangular sidefacing cutting windows 106 and 108, respectively, formed in the annular walls near their distal ends. Shapes other than rectangular or rectilinear may also be suitable. The inner cutting window 106 is formed of a pair of parallel, longitudinally extending, sharpened edges 110 and 111 and a pair of parallel, transversely extending arcuate edges 112 and 113. Outer cutting window 108 is formed of a pair of parallel, longitudinally extending radiused edges 115 and 116 and a pair of transversely extending arcuate edges 117 and 118. The distal-most edges 113 and 118 of both windows are longitudinally spaced from the distal tip 120 by a predetermined distance sufficient to enable formation in both inner and outer distal tips of hemispherical ends 122 and 124. The outer surface of end 124 and the inner surface of end 122 cooperate as bearing surfaces in a conventional manner. The blunt hemispherical ends 122 and 124 enable the liposhaver blade to pass through adipose tissue safely.

In plan view, the outer cutting window 108 resembles a rectangular aperture of a conventional liposuction cannula. The longitudinally extending edges 115 and 116 of the outer member are fully radiused as shown in FIG. 3 in order to avoid any inadvertent injury to adjacent tissue. In the preferred embodiment, edges 110 and 111 are sharpened and lie on a common radius of curvature (or they may simply be angled relative to a radius from the axis of the inner member). The transverse edges of the inner and outer windows may be intentionally dulled or may be left as straight cuts through the side walls (but are not sharpened per se). While all edges are shown to be straight, various edge shapes (e.g. sinusoidal, undulating, etc.) may be used without departing from the scope of the invention.

It will be understood that as the inner member rotates or oscillates within the outer member the edges 110 and 111 alternatively approach and pass edges 115 and 116 in a parallel fashion in order to slice any tissue presented in outer window 108. This is known as an orthogonal cut and it is noted that in such a cut there is no angled shearing action as in a pair of scissors and in some prior art resecting shavers. While both windows are larger than prior art shavers, the size of the inner window 106 is larger than window 108 as shown in FIG. 2 in order to assure that, when the inner and outer members are aligned as explained below, the sharp inner edges 110, 111 are recessed below outer edges 115, 116 to avoid injury to adjacent tissue. The parallel alignment of the inner edges relative to the outer edges facilitates use of the instrument in either a manual or powered manner, although a non-parallel arrangement may be suitable without departing from the scope of this invention.

As with other shavers, it will be understood that the relationship between the size of the rectangular cutting window, rotation speed and the amount of suction is a parameter to be considered in the design and use of the instrument. Too large a window or too much suction may produce either clogging or uncontrolled resection. In the preferred embodiment, when the outside diameter of the outer tube is 3.5 mm (0.126 inches), the depth D of the outer window may be 0.053 inches, the window length L may be 0.120 inches and the window setback S may be 0.078 inches. The inner window has corresponding dimensions of 0.050 inches, 0.150 inches and 0.050 inches, respectively. If the outer tube diameter is 4.2 mm (0.158 inches), the outer tube window depth, length and setback are 0.094 inches, 0.150 inches and 0.094 inches, respectively, and the corresponding inner tube parameters are 0.065 inches, 0.180 inches and 0.065 inches, respectively. The windows of both inner and outer tubular members or, more accurately, the edges defining the windows, lie in an axial plane near the axis of the respective tube. This is referred to as the diametral region and this window placement optimizes the size of window for any particular tube diameter.

When it becomes necessary or desirable during a surgical procedure for removal of adipose tissue to temporarily stop the cutting, lipectomy action of the liposhaver assembly the user may rely solely on aspiration as in a conventional liposuction cannula. This may be done with liposhaver instrument 100 by aligning the inner and outer windows in an open position as shown in FIG. 2 thereby leaving the inner lumen aperture open to allow the aspiration of tissue without cutting. A system for doing this by stopping the motion of the inner member relative to the outer member is described in a co-pending application assigned to the assignee hereof and incorporated by reference herein. This system enables the size of the opening at the distal tip of the assembly, i.e. the entry of the lumen of the inner member or lumen aperture, to be maximized to improve the efficiency of aspiration during those times when the surgeon wants to use the shaver assembly for aspiration only. Such control would also enable the inner member to be stopped in a closed position to prevent aspiration and permit use of the liposhaver as a simple probe. Obviously any intermediate degree of window openness (i.e., alignment) may be selected if a user so chooses, although this would expose a sharp edge of the inner window and is, therefore, a mode which should be used cautiously.

It will be understood by those skilled in the art that numerous improvements and modifications may be made to the preferred embodiment of the invention disclosed herein without departing from the spirit and scope thereof.

What is claimed is:

1. A surgical resection instrument for use with a powered handpiece comprising:

an elongated outer tubular member having a generally rounded distal end, a proximal end with a hub for fixed attachment to said handpiece, said outer member having a first rectangular cutting window spaced a predetermined distance from its distal end, said rectangular cutting window comprising an opening formed in the side wall of said outer member by a first transverse edge extending diametrically across said outer member, a second transverse edge parallel to and longitudinally spaced from said first transverse edge and equal in length thereto, a third, longitudinally extending edge joining corresponding ends of said first and second transverse edges and a fourth, longitudinally extending edge parallel to and transversely spaced from said third edge and equal in length thereto; and an elongated inner tubular member received within said outer tubular member and having a generally rounded distal end, a proximal end with a hub for rotatable attachment to said handpiece, said inner member having a second rectangular cutting window spaced a predetermined distance from its distal end, said first and second rectangular cutting windows being symmetrical to and situated adjacent each other, said second rectangular cutting window comprising an opening formed in the side wall of said inner member by a fifth transverse edge extending diametrically across said inner member, a sixth transverse edge parallel to and longitudinally spaced from said fifth transverse edge and equal in length thereto, a seventh, longitudinally extending edge joining corresponding ends of said fifth and sixth transverse edges and an eighth, longitudinally extending edge parallel to and transversely spaced from said fourth edge and equal in length thereto.

2. A surgical resecting instrument according to claim 1 wherein said longitudinal edges of said outer member rectangular cutting window are rounded.

3. A surgical resecting instrument according to claim 1 wherein said edges of said inner member are sharpened.

4. A surgical resecting instrument according to claim 1 wherein all edges of said first and second rectangular cutting windows lie in a plane parallel to the axis of the respective tubular member and within the diametral region thereof.

5. A surgical resecting instrument according to claim 1 wherein, when said first and second rectangular cutting windows are aligned in an open position, said longitudinal edges of said second rectangular cutting window are spaced below said longitudinal edges of said first rectangular cutting window.

6. A surgical resecting instrument according to claim 1 wherein said generally rounded distal ends of said inner and outer members are substantially hemispherical with the distal-most one of said transverse edges being situated at or proximal to the diameter of the hemisphere.

* * * * *